United States Patent
Campbell

(10) Patent No.: US 7,219,534 B2
(45) Date of Patent: May 22, 2007

(54) METHOD AND APPARATUS FOR DETERMINING TRANSPIRATION CHARACTERISTICS OF A PERMEABLE MEMBRANE

(75) Inventor: Michael J. E. Campbell, Merideth, NH (US)

(73) Assignee: Nova Technology Corporation, Portsmouth, NH (US)

( * ) Notice: Subject to any disclaimer, the term of this patent is extended or adjusted under 35 U.S.C. 154(b) by 0 days.

(21) Appl. No.: 10/906,761

(22) Filed: Mar. 4, 2005

(65) Prior Publication Data

US 2006/0254341 A1 Nov. 16, 2006

(51) Int. Cl.
G01N 15/08 (2006.01)
(52) U.S. Cl. ............................................. 73/38; 73/73
(58) Field of Classification Search ............... None
See application file for complete search history.

(56) References Cited

U.S. PATENT DOCUMENTS

| | | | | |
|---|---|---|---|---|
| 4,862,730 | A * | 9/1989 | Crosby | 73/38 |
| 5,390,539 | A * | 2/1995 | Mayer | 73/38 |
| 6,595,042 | B2 * | 7/2003 | Holliday et al. | 73/64.47 |
| 2002/0162384 | A1* | 11/2002 | Sharp et al. | 73/38 |

FOREIGN PATENT DOCUMENTS

| EP | 0435432 A | 3/1991 |
|---|---|---|
| EP | 1072880 A1 | 1/2001 |
| JP | 2001289764 | 10/2001 |

OTHER PUBLICATIONS

Morhenn and Palenske, A Wound Healing Study in Humans Using the Nova DPM 9003, The Nova Techonology Corp. Newsletter, Summer 1997.
Rizer et al., The Use of the NOVA DPM 9003 with Measure Delay Option for Characterizing the Skin Effects of a Novel Delivery System compared to a Marketed Retinoid.
The Nova Technology Newsletter, Spring 1999.
www.adhesiveresearch.com/medical/amedwoun.htm#thinfilm.
Goretsky et al., Surface Electrical Capacitance as an Index of Epidermal Barrier Properties of Composite Skin Substitutes and Skin Autografts.
Wound Repair and Regeneratin, vol. 3, No. 4.
Miller, David L., Skin Stripping ELectrical Properties of Stratum Corneum, Demral Clinical Evaluations Society Poster Session, Jun. 1991.
Jackson, et al., The Use of Atopics and Adhesive-Sensitive Panelists to Assess a New Sensitive-Skin Bandage, Cosmetic Dermatology, vol. 7, No. 11, Nov. 1994.
DPM 9003-Dermatological Laboratory Instrument, Specification Sheet, Nova Technology Corporation.

* cited by examiner

*Primary Examiner*—Hezron Williams
*Assistant Examiner*—Paul M. West
(74) *Attorney, Agent, or Firm*—George A. Herbster

(57) ABSTRACT

A system and method for measuring the transpirational characteristics of a permeable polymeric membrane, particularly polymeric membranes used for bandages. The polymeric membrane is placed against a moisture source. A probe is applied to the other side. Signals from the probe are sampled at a high rate to detect a first transient appearance of moisture on the surface being measured. The interval between the first transient response and a predetermined equilibrium value defines the transpirational characteristics of the polymeric membrane.

7 Claims, 8 Drawing Sheets

METHOD AND APPARATUS FOR DETERMINING TRANSPIRATION CHARACTERISTICS OF A PERMEABLE MEMBRANE

FIELD OF THE INVENTION

This invention generally relates to the measurement of transpiration through a permeable membrane and more specifically to the prediction of transpiration properties of polymer materials useful as bandages during wound healing and useful in other applications.

DESCRIPTION OF RELATED ART

For a significant time standard dogma held that air drying a skin wound promoted healing. More recently, however, it has been determined that partially occluding a wound may accelerate healing because a partial occlusion prevents migration of the epidermis into the dermis to seek moisture. It has also been found that a complete or full occlusion leads to skin maceration that, in turn, adversely affects wound healing. Consequently efforts are underway to identify materials that can control the moisture at a wound site. Maceration can also be a factor in other situations. For example, if a polymer bandage that holds an IV in place has poor migration characteristics, maceration under the bandage may cause skin damage, especially to premature babies.

One promising effort involves the development of a variety of polymer-based membranes that have the potential to improve wound healing or to minimize skin damage by controlling the moisture level from the skin under the bandage. During these studies it has become evident that the transport mechanism by which moisture passes through such bandages varies widely with different materials, so it has been difficult to predict these characteristics without actual use.

One approach or procedure by which this characteristic of different materials can be evaluated and categorized uses stripping. Initial testing includes the step of tape stripping until the epidermis shows signs of "glistening". This visual test is subjective. It is difficult to obtain repeatable quantitative information with this process. If such a repeatable process were available, the development of enhanced polymer and other bandages could be enhanced. Consequently, there still is a need for a method and apparatus that will predict the transpiration characteristics of such bandages.

SUMMARY

Therefore, it is an object of this invention to provide a method and apparatus for providing a repeatable quantitative evaluation of the wound healing capabilities of polymer based bandages.

Another object of this invention is to provide a method and apparatus for providing a quantitative evaluation of the transpiration characteristics of a polymer-based bandage.

Still another object of this invention is to provide a method and apparatus for providing a quantitative evaluation of the transpiration characteristics of a polymer-based bandage that will predict its efficacy in wound healing.

In accordance with this invention the transpiration characteristics of a permeable membrane includes placing a first surface of permeable membrane on a moisture source. The second surface is then sampled on an iterative basis to detect a first transient appearance of moisture at that surface. The time measured from the first transient appearance of moisture to a predetermined moisture level at the second surface defines a transpiration characteristic of the permeable membrane.

BRIEF DESCRIPTION OF THE DRAWINGS

The appended claims particularly point out and distinctly claim the subject matter of this invention. The various objects, advantages and novel features of this invention will be more fully apparent from a reading of the following detailed description in conjunction with the accompanying drawings in which like reference numerals refer to like parts, and in which:

DESCRIPTION OF ILLUSTRATIVE EMBODIMENTS

Figure 1:
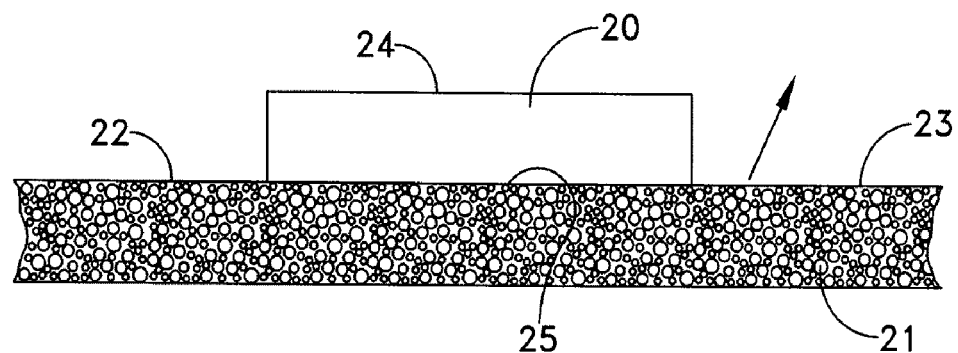
FIGS. 1 through 3 are useful is understanding the mechanism by which moisture passes through a polymer bandage.
Figure 2:
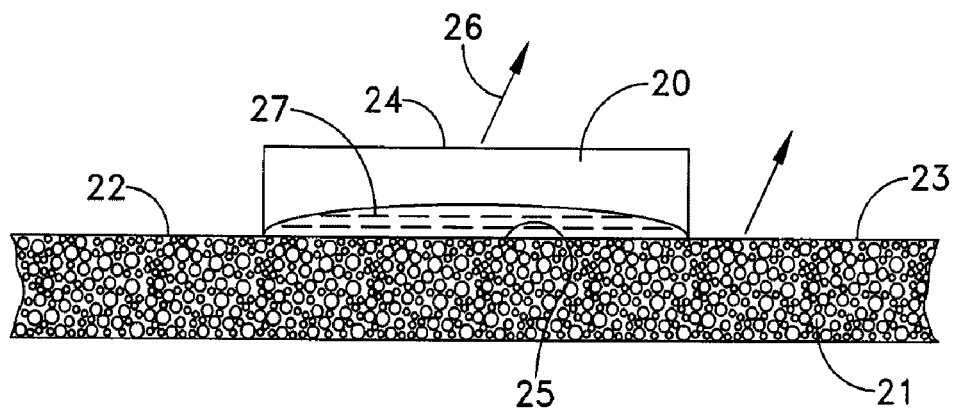
Figure 3:
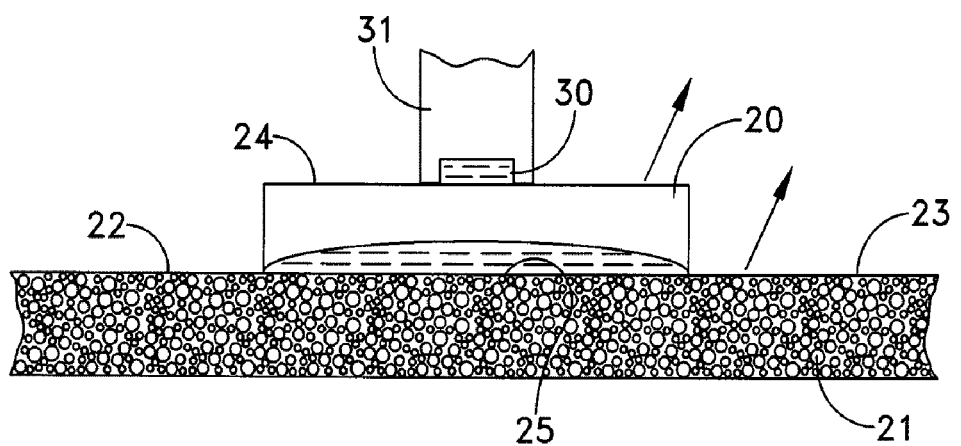

As background to an understanding of this invention, FIGS. 1 through 3 depict a permeable membrane in the form of a polymer bandage material 20 overlying an epidural layer 21. At a first application of the polymer bandage 20 to the epidural layer 21, shown in FIG. 1, moisture evaporates from the non-occluded surfaces 22 and 23. Immediately upon application, however, an outer or second surface 24 of the polymer layer is dry.

After some time, as shown in FIG. 2, the area 25 occluded by the bandage 20 begins to accumulate moisture. During this interval some of this moisture periodically migrates to the surface 24 on a transient basis as represented by arrow 26 The transient interval may only be in the millisecond time domain. This transient phase exists even though there may be a continuous accumulation of moisture in the occluded area 27 between the bandage 20 and the epidermal layer 21.

FIG. 3 depicts a step of evaluating the moisture content of the surface 24 by defining an occluded area 30 with a probe 31 at some time after the stage shown in FIG. 2. By this time, moisture accumulates in the occluded area 30 even though parallel evaporation of moisture from the surface 24 continues.

Figure 4:
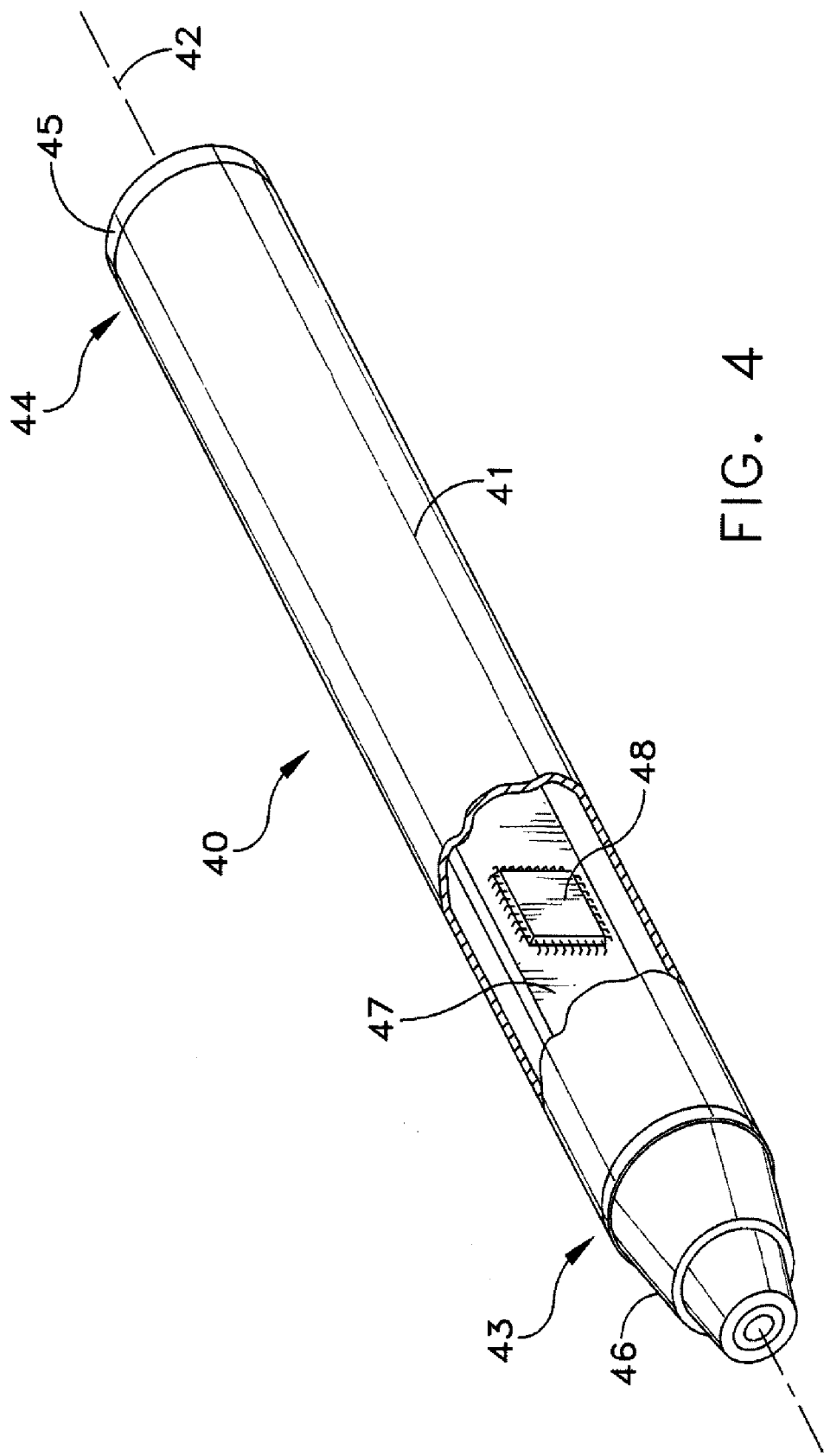
FIG. 4 is a perspective view of a probe that provides a measurement of skin impedance for determining the transpiration characteristics of a polymer bandage.

FIG. 4 depicts a preferred embodiment of a probe 40 that is useful in accumulating data for this invention. The probe 40 contains a cylindrical housing 41 lying along an axis 42 between a first, distal end 43 and a second, proximal end 44. In the case of the probe 40 "distal" is meant to refer to the end that is most the proximate the patient. A connector 45 closes the proximal end 44 of the probe housing 41. The distal end 43 of the probe housing 41 carries a sensor body 46. In this particular embodiment the probe housing 41 also carries a printed circuit board 47 with a number of components represented by an integrated circuit 48. The components on the printed circuit board perform various functions including those disclosed in FIG. 5. In this specific embodiment, the printed circuit board 47 includes other components (not shown) for operating the probe 40 as a self-contained, battery operated measurement system. The end connector 45 provides a data path for downloading data to a conventional personal computer system for analyzing the data and evaluating the transpiration characteristics of a polymer bandage or membrane.

Figure 5:
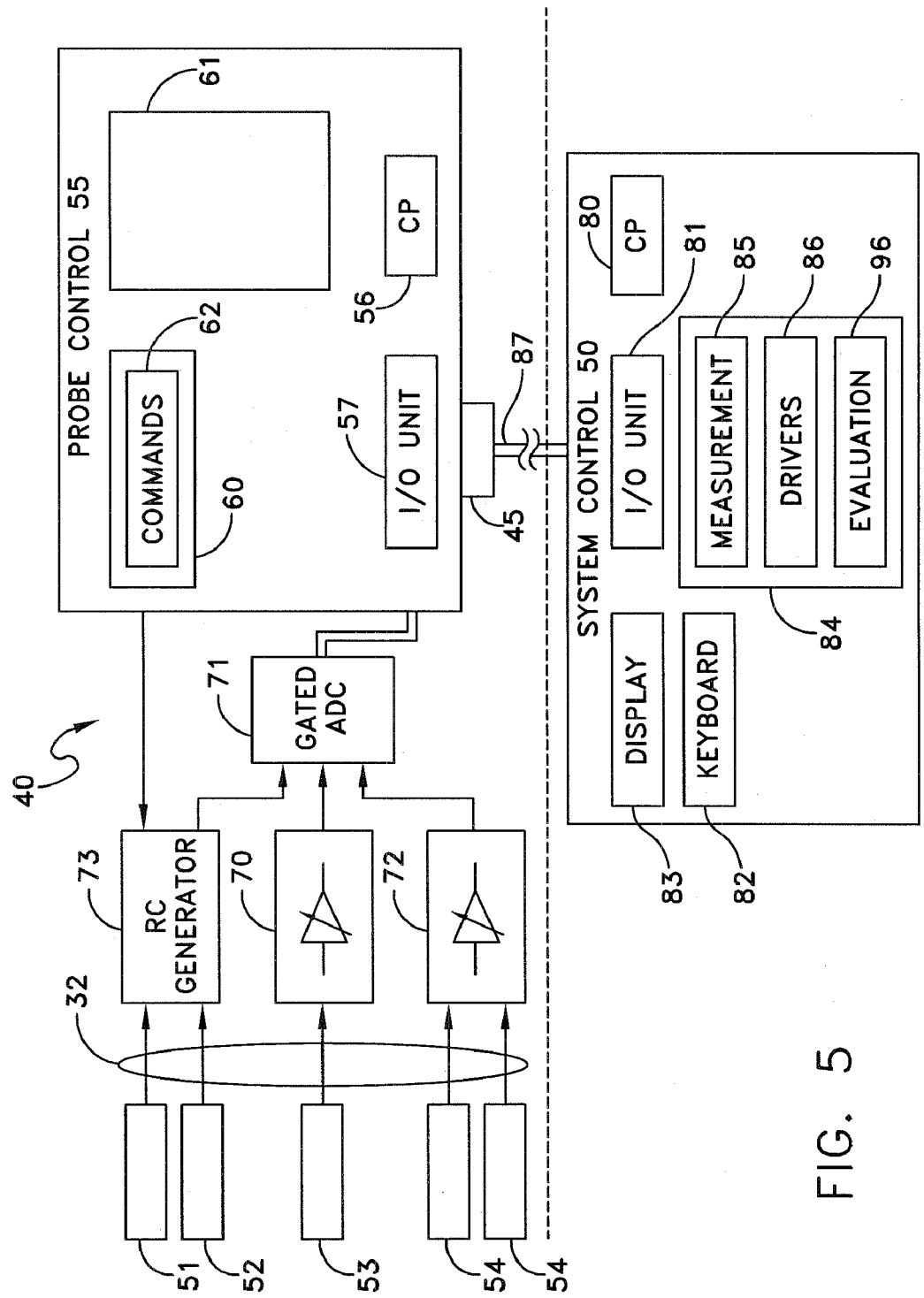
FIG. 5 is a block schematic diagram of circuitry for implementing this invention in conjunction with the probe of FIG. 4.

FIG. 5 depicts the probe 40 and an associated data processing system or system control 50 that provide a transpiration analysis in response to the signals from the electrodes 51 and 52. This probe 40 also includes a thermocouple 53 and force transducers 54 for providing additional information and for increasing the accuracy of moisture readings sent to the system control 50 that can comprise any conventional personal computer or laptop with an input/output interface such as an RS232 interface.

Within the probe 40 itself, a probe control 55 attaches to the connector 45 to receive signals from and transfer data to the system control 50. More specifically, the probe control 55 comprises a conventional micro-processor or other central processing system that includes a central processor (CP) 56, an I/O unit 57, a memory 60 and a second memory 61 typically implemented as in EPROM or other form of programmable read only memory. The probe control 55 produces moisture signals in response to specific commands from the system control 50. The memory 60 includes modules or programs 62 for responding to such commands and buffers that are not specifically shown.

Any number of circuits exist for providing a signal that indicates the moisture content. This probe uses an RC generator 73 that responds to successive initiation signals from the probe control 55 to generate a signal having an RC time constant that is applied as one input to the gated ADC 71. In the system depicted in FIG. 5, a voltage pulse is applied to an RC circuit with the electrodes 51 being in parallel with the RC circuit. The pulse has a fixed value and a duration exceeding a predetermined time. The initiation signal enables the RC generator to apply a reference signal to the gated ADC 71 and then to apply the capacitor voltage to the gated ADC. In accordance with this invention, the gated ADC 71 operates at a high sampling frequency (e.g., greater than 10 or more samples per second) and is able to obtain voltage measurements over the rise time of the voltage of the capacitor. Each sample then represents the measurement of the complex impedance with a quantification of the capacitive reactance that is an indicator of substrate moisture.

The system control 50 comprises a personal computer or laptop that includes a central processor 80, an I/O unit 81, an input keyboard or keypad 82 and a display 83. A memory 84 contains, among other items, a measurement module or program 85 and various drivers 86. The measurement module 85 generates commands including, particularly, a TAKE SAMPLES command that initiates the process for obtaining information from the RC generator 73. These commands are communicated over a bus, such as a serial RS-232 bus 87 from a serial I/O port and the connector 45 to be received in the probe control 55. In response the probe control 55 begins to sample the signals from the RC generator 73 as may optionally be modified by temperature and force measurements.

During the measurement process data streams across the interface to the system control 50 at this high rate. In one embodiment, the transfer rate is 9600 baud. The system control 50 periodically samples this data stream and asynchronously and then generates, for each sample, a moisture reading and a time stamp. This information can then be combined with other data such as patient identification, operating parameters, etc. to produce a table recording each reading the system control samples.

Figure 6:
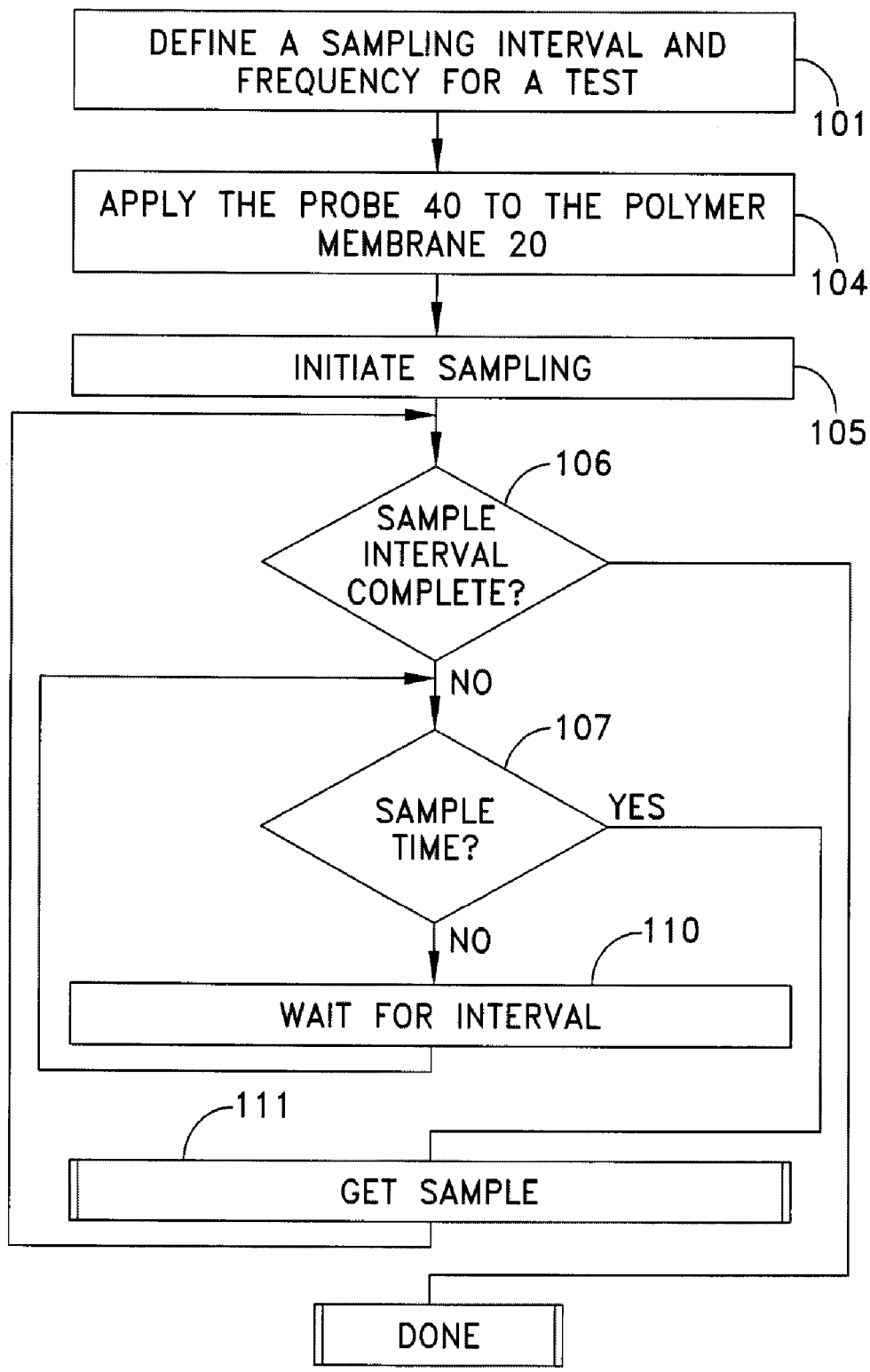
FIGS. 6 through 8 are flow charts and a map that illustrate the operation of the circuitry in FIG. 5 for enabling the measurement of the transpiration characteristics of a polymer bandage.
Figure 7:
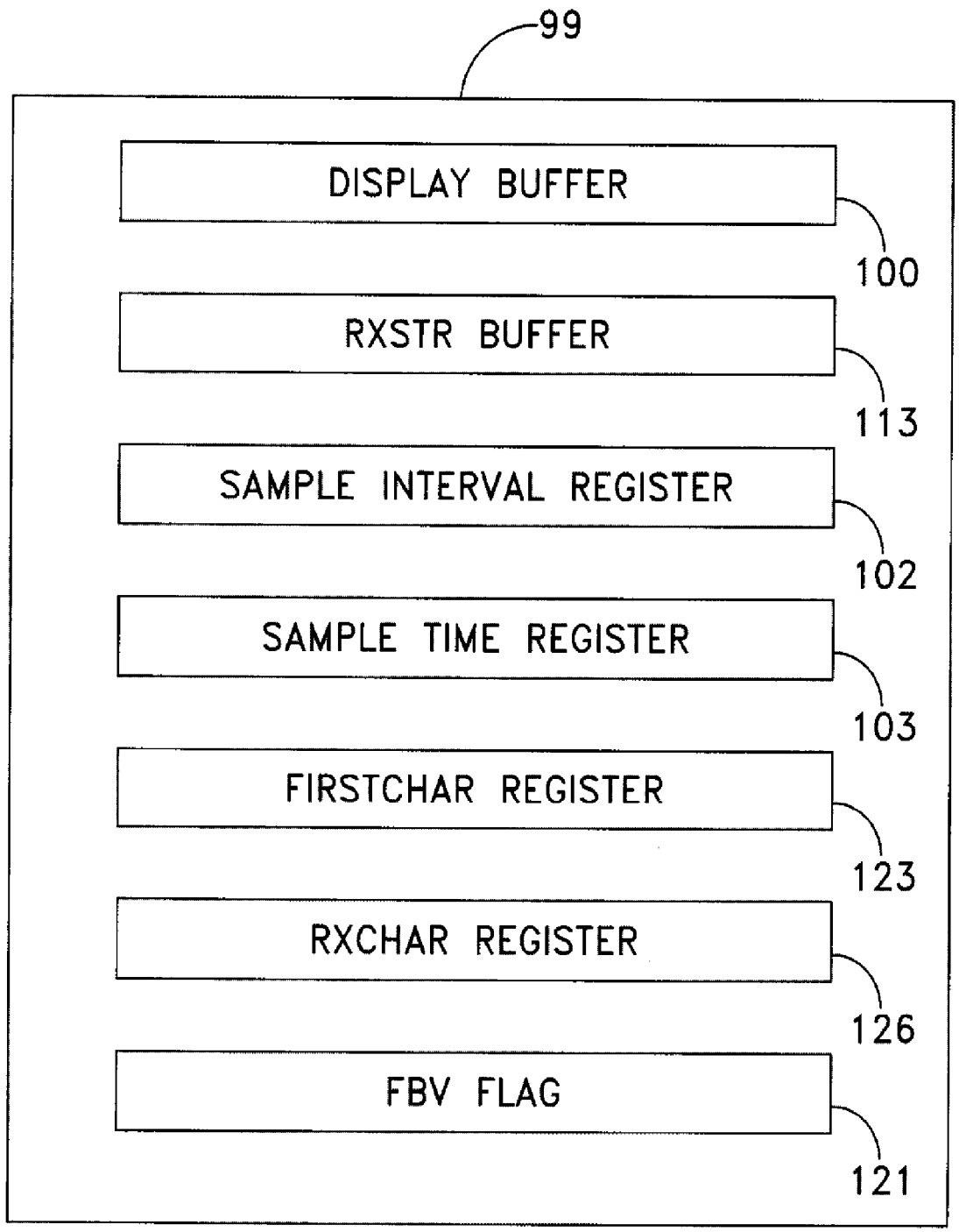

FIG. 6 outlines the operation of the system control 50 in obtaining samples for transfer into a map 99 in FIG. 7 that comprises a set of requests including a display buffer 100. The map 99 of FIG. 7 forms a portion of the measurement module 85 in FIG. 5. FIG. 7 depicts various other buffers, registers and flags useful in understanding the operation of FIGS. 6 and 8 as will become apparent.

Referring to FIG. 6, step 101 enables a user to define a sampling interval and sampling frequency for a test. These values are stored in registers 102 and 103 in FIG. 7. Next a probe, such as the probe 40 shown in FIG. 1 is applied to a polymer or like membrane in step 104, such as the membrane 20 in FIGS. 1 through 3, that overlies a supply of moisture. Step 105 initiates sampling. Sampling may actually begin immediately upon the application of the sensor. If a priori knowledge indicates that certain delays will exist before a transient appears, the initiation of sampling could be deferred for a corresponding interval. Essentially, the sampling should be initiated at least just before it is expected that a first moisture transient will appear on the surface 24 in FIGS. 1 through 3. Such delays permit the system to record only relevant data and avoid recording and storing data that will be irrelevant.

Step 106 determines whether the sampling interval is complete. Immediately after step 105 has been processed, control will pass from step 106 to step 107 to determine if sample time has been reached according to the value stored in register 103. Steps 107 and 110 operate as a loop whereby step 110 introduces an incremental time delay and passes control back to step 107. When it is time to take a sample, control passes from step 107 to a routine 111 that processes the data stream from the probe control 55 to obtain a moisture value.

The loop comprising steps 106 through 111 constitutes a first iterative process and continues until the sample interval defined in register 102 in FIG. 7 is completed. Then step 106 terminates the sampling process. After that, the system control 50 can process the information in the display buffer 100 to provide a quantitative and/or graphical analysis and determine the transpirational characteristics for the sample.

Figure 8:
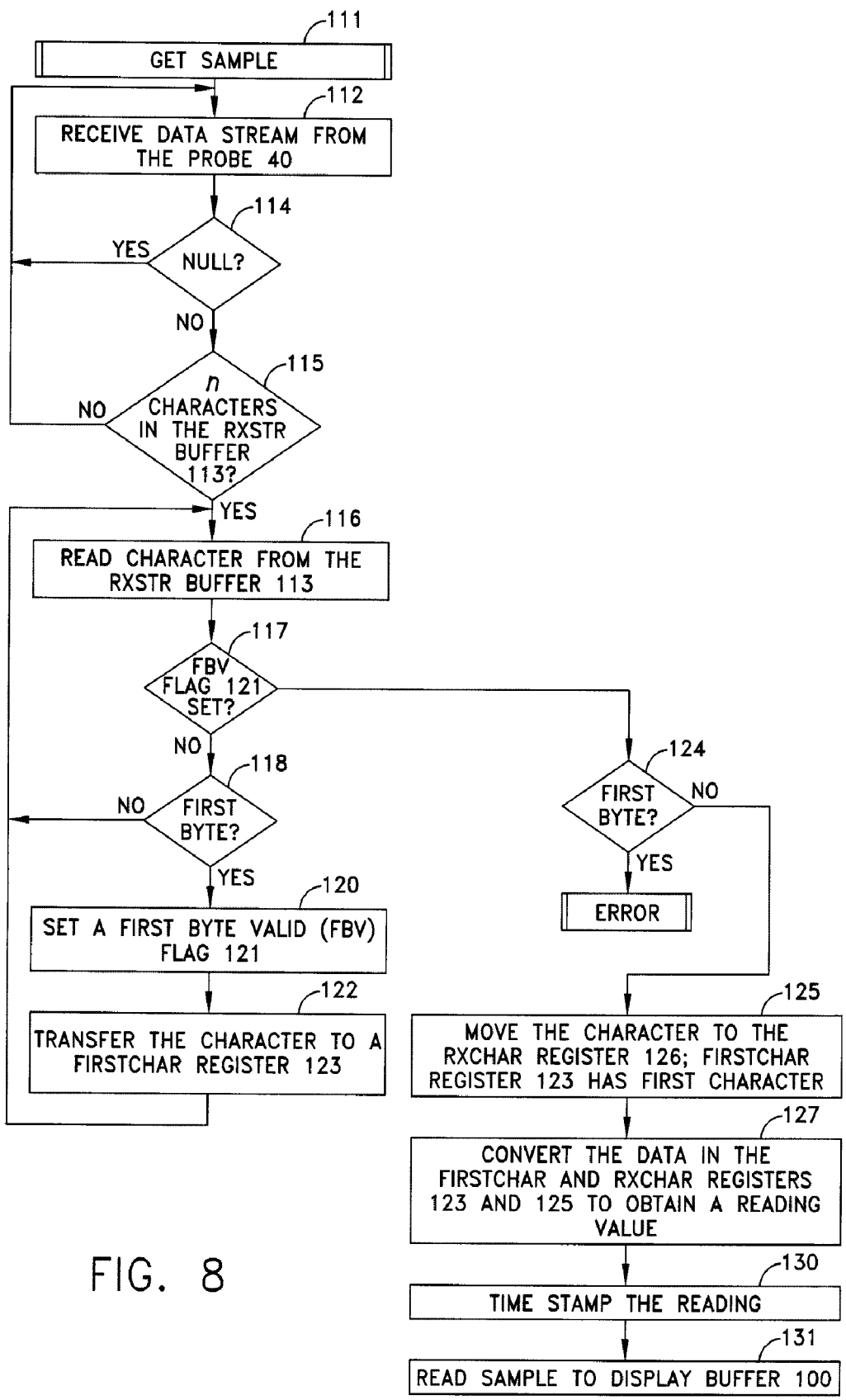

As previously indicated, in one embodiment of this invention, the data transfer rate across the path 87 in FIG. 5 is significantly greater than the required sampling rate even for the shortest transient moisture intervals. In one specific embodiment, each data reading transfers across the path 87 as an encoded 16-bit, or 2-byte, transfer in a continuous data stream. The GET SAMPLE routine 111 in FIG. 8 is a second iterative process. When called from step 111 in FIG. 6, this GET SAMPLE routine retrieves data from this stream until it obtains a valid 2-byte pair. The routine then converts this pair into a decimal reading and records the reading with a time stamp.

Still referring to FIGS. 7 and 8, step 112 represents the receipt of data from the probe control 55 in FIG. 5 over the path 87 into a received string (RXSTR) buffer 113. The routine 111 monitors this stream for a non-null value in step 114 of FIG. 8. When a character is received, step 115 determines how many characters are in the RXSTR buffer 113. There should be a minimum number of characters, n characters, in the RXSTR buffer 113 to assure that a specific instance of the GET SAMPLE routine has sufficient data. In a preferred embodiment step 115 transfers control to step 116 when three or more characters are present in the RXSTR buffer 113.

If there are fewer than the predetermined number of bytes in the RXSTR buffer 113, step 115 transfers control back to step 112 and this loop continues until the RXSTR buffer 113 contains the requisite number of bytes. During active sampling the time required to accumulate the requisite number of bits will be less than the system control sampling interval. When this occurs, step 116 reads a character from RXSTR buffer 113. If step 117 determines that a byte is marked as a first character, control passes to step 120 that sets a first byte valid (FBV) flag 121 shown in FIG. 7. Step 122 then transfers that data byte to a FIRST CHAR register 123.

When a subsequent character is read in step 116 and the FBV flag 121 is set, control transfers from step 116 through step 117 to step 124 that tests the incoming character for the first character mark. Normally the following character will not be marked as it will be a second character, so step 124 transfers control to step 125 that moves the second character to an RXCHAR register 126. Step 127 converts the data in the FIRST CHAR and RXCHAR registers 123 and 126 into a reading that is compatible for the remainder of the system.

For example, if the data from the probe control 55 in FIG. 5 is generated as 2-byte encoded value, step 127 converts this encoded data into a decimal value. Step 130 then appends a time stamp and the information including the time stamp and the reading transfer to the display buffer 100 in step 131. When this process completes, the procedure 111 has been completed and control passes back to step 106 in FIG. 6 to test the time interval and enable another sample to be taken. Thus each time the procedure in FIG. 8 executes, one data value will be obtained from the data stream. As will also be apparent, if the sampling frequency for the system control 50 is less than that for the probe control 55 in FIG. 5, only a portion of the data sent to the system control 50 will be processed. This reduces the load on the resources available in the system control 50 so that the system control 50 can perform other functions in parallel with the sampling process.

If the first character step 116 is a second character, it is discarded. Steps 117 and 118 will transfer control back to step 116 to read a next character. That next character should be marked as a first character whereupon steps 117, 118, 120 and 122 transfer that character to the FIRST CHAR register 123.

Figure 9:
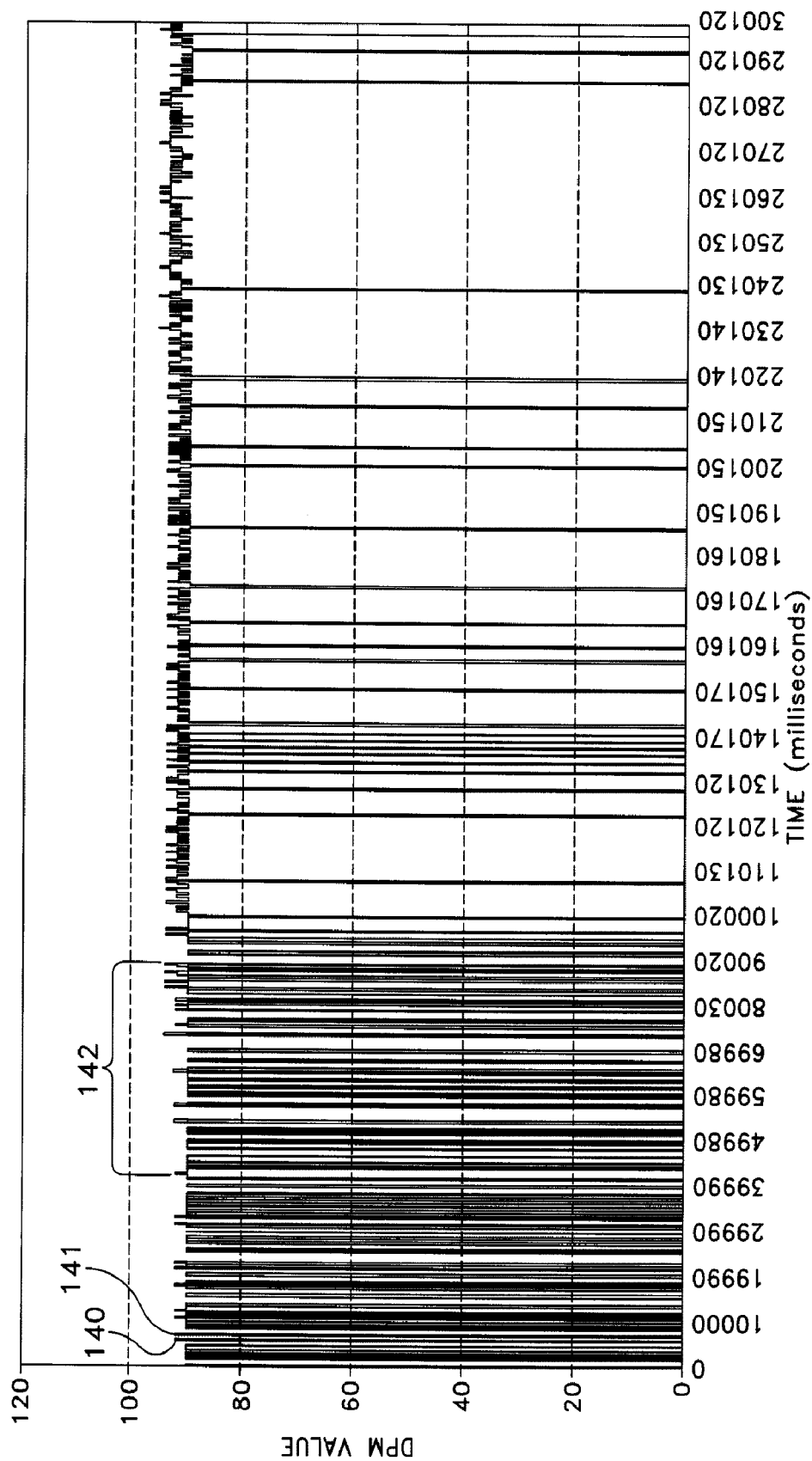
FIGS. 9 and 10 are graphical representations of the quantitative data from a measurement of two different polymer membranes obtained by using this invention.
Figure 10:
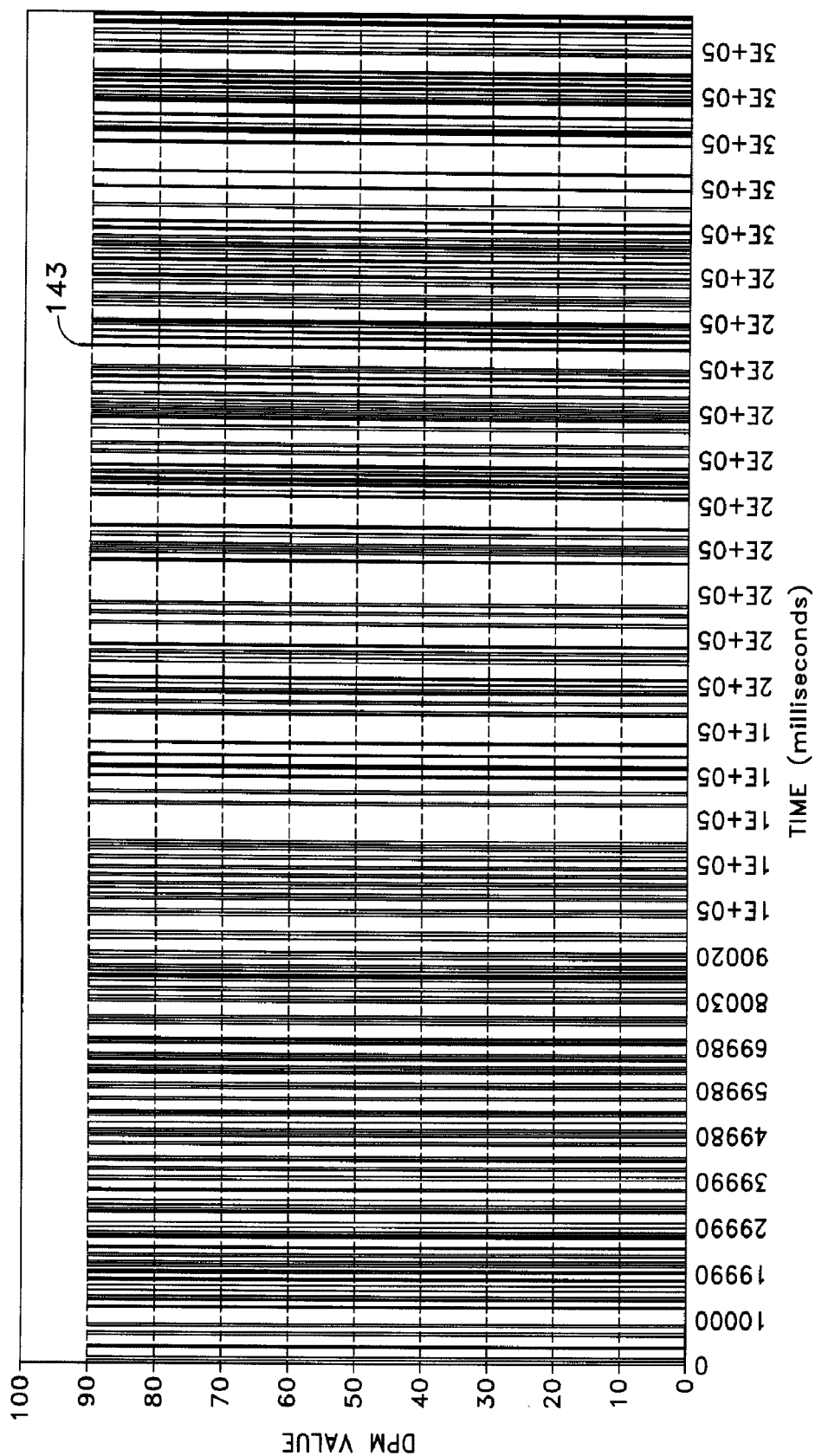

FIGS. 9 and 10 depict plots of the individual readings as a function as time over five minute samples starting after some occlusion time. In FIG. 9, the appearance of a first transient occurs at 140, the first time the reading exceeds a threshold value. In this specific embodiment, for reasons that are not important to this invention, the probe control 55 in FIG. 5 generates a minimum reading of 90 that constitutes a "0" moisture reading.

Still referring to FIG. 9, at about 7 seconds the first transient response appears as a reading above 90 followed about a millisecond later by a second transient response 141. These intermittent or transient responses continue up to a region 142 beginning at about 40 seconds and extending to 90 seconds. Over this range the frequency and amplitude of the transient responses begin to increase. Beyond the region 142, more moisture accumulates and the readings continue to increase both in frequency and in magnitude until an equilibrium condition exists.

Assuming that $t_t$ is the time of the appearance of the first transient at position 140 in FIG. 9, that $DPM_{eq}$ represents the difference from the zero moisture ready to an equilibrium reading from the instrument, that k is a proportionality constant and that $tk\, DPM_{eq}$ represents the time at which the readings reach a value corresponding to k $DPM_{eq}$, the transpirational constant (TC), is given by:

$$TC = \frac{kDPM_{eq}}{t_{kDPM_{eq}} - t_t}$$

where $0 \leq k \leq 1$. A value k=0.63 has been found to produce a good, repeatable characteristic.

FIG. 10 presents data from a membrane that enables essentially no moisture to migrate. Consequently, there is only one transient response 143 in the sample period. Thus it will be obvious comparing FIGS. 9 and 10 that this procedure provides different data for materials with different permeability. Moreover, these results are repeatable so the rise time, represented by TC, reliably predicts the efficacy of a polymer material as a bandage. Such a test enables manufacturers to evaluate different compositions and to control the permeability thereby to more carefully control the evaporation of moisture from the wound and skin in proportion to the way in which an individual normally evaporates perspiration from the skin.

Referring to FIG. 9, if the sampling rate were to decrease, the accuracy of $t_t$ would decrease because location of a sampled first transient would likely shift to the right in FIG. 9. Such a shift can produce a significant increase in the value of TC because it has a first order effect on the accuracy of the slope provided by Equation (1). Slower sampling rates have less impact on the accuracy of the TC value. As the moisture level increases, any variance of the $tDPM_{eq}$ value will be reasonably small as a function of sampling rate. The result of inaccuracies in this measurement of $tDPM_{eq}$ will produce changes in the slope that are more closely second order changes. Consequently, the selected sampling rate should be selected to assure the accurate detection of the first transient response. It has been found that 10 samples per second provide a reasonable sampling rate for most bandage materials that have been tested. Higher or lower sampling rates may be selected for other specific applications.

This invention has been disclosed in the context of a system with a particular probe control for measuring surface moisture with a process for monitoring and analyze those measurements. It will be apparent to those of ordinary skill in the art that such a system could be implemented in other diverse ways using other packaging concepts, by moving certain components from one component to another in FIG. 5 and by using alternate analysis of the data stream depending upon the particular data stream syntax. Therefore, it is the intent of the appended claims to cover all such variations and modifications as come within the true spirit and scope of this invention.

What is claimed is:

1. A method for measuring the transpiration characteristics of a permeable membrane having first and second surfaces comprising the steps of:
   A) attaching the permeable membrane to a site that is a source of water evaporation with the first surface facing the site,
   B) iteratively sampling the second surface for the determining the accumulation level of moisture at the second surface, and
   C) measuring the time from a first transient appearance of moisture to the time of the accumulation of a predetermined moisture level at the second surface, the measured time constituting a transpiration characteristic of the permeable membrane wherein said time measurement includes the steps of:
i) measuring the equilibrium value of moisture on the second surface,
ii) establishing a threshold value as a percentage of said measured equilibrium value, and
iii) said time measuring extending from the time from the first transient appearance of moisture until the moisture value reaches a predetermined percentage of the equilibrium value.

2. A method as recited in claim 1 wherein said threshold value establishment includes establishing a percentage of 63% of the equilibrium value.

3. A method as recited in claim 1 wherein said first transient has a characteristic time duration and said equilibrium value measurement includes discretely sampling the impedance of an occluded portion of the second surface at a sampling interval that is less than the characteristic time duration.

4. A method as recited in claim 3 wherein said iterative sampling includes a first iterative sampling process at a first sampling frequency for obtaining measurements of the moisture at the second membrane surface and a second iterative sampling process at a second sampling frequency for sampling the measurements obtained in the first iterative sample process.

5. A method as recited in claim 4 wherein the second sampling frequency is less than the first sampling frequency.

6. A method as recited in claim 4 wherein said sampling additionally includes recording a time and impedance value for each sample obtained during the second sampling process.

7. A method as recited in claim 6 wherein said time measurement includes analyzing the recorded time and impedance values for each sample during the second sampling process.

* * * * *